United States Patent
Huang et al.

(10) Patent No.: US 8,538,983 B2
(45) Date of Patent: Sep. 17, 2013

(54) SYSTEMS, METHODS, AND APPARATUS FOR FACILITATING CHEMICAL ANALYSES

(75) Inventors: Biying Huang, Apex, NC (US); Scott Gregory Flicker, Raleigh, NC (US); William B. Ballard, Raleigh, NC (US); Robin Young Smith, Boston, MA (US); Sean Gerard Greenhow, Raleigh, NC (US); Shadrack Cgar Frazier, Durham, NC (US)

(73) Assignee: CambridgeSoft Corporation, Waltham, MA (US)

( * ) Notice: Subject to any disclaimer, the term of this patent is extended or adjusted under 35 U.S.C. 154(b) by 0 days.

(21) Appl. No.: 13/239,069

(22) Filed: Sep. 21, 2011

(65) Prior Publication Data

US 2012/0078853 A1   Mar. 29, 2012

Related U.S. Application Data

(60) Provisional application No. 61/384,822, filed on Sep. 21, 2010.

(51) Int. Cl.
*G06F 17/30* (2006.01)

(52) U.S. Cl.
USPC ............................. 707/769; 707/708

(58) Field of Classification Search
None
See application file for complete search history.

(56) References Cited

U.S. PATENT DOCUMENTS

| | | | |
|---|---|---|---|
| 7,650,327 B2 | 1/2010 | Remsen et al. | |
| 2004/0003000 A1* | 1/2004 | Smith et al. | 707/104.1 |
| 2006/0277201 A1* | 12/2006 | Dorsett, Jr. | 707/10 |

* cited by examiner

*Primary Examiner* — Pierre Vital
*Assistant Examiner* — David T Brooks
(74) *Attorney, Agent, or Firm* — Choate, Hall & Stewart, LLP

(57) ABSTRACT

A knowledge management platform eliminates the trial and error process for analytical chemists in, for example, identifying appropriate methodologies for separating mixtures of chemical compounds. The platform allows the analytical chemists to perform a variety of searches on data existing from previous experiments, procedures, and/or processes. The platform may be employed to make faster decisions, and ultimately decreases the time taken in selecting an appropriate separation methodology.

20 Claims, 8 Drawing Sheets

FIG. 2

Welcome, katel Logout     Method Search Results     Return to search

Structure Properties

| Compound | IU PAC Name | Weight | CLogP | Molar Volume | Info |
|---|---|---|---|---|---|
| 0868554 | (6R)- | 503.637 | 4.627 | 388.803 | ⊖ |
| 4343801 | (4S)- | 177.2 | 1.325 | 150.591 | ⊖ |
| 0248529 | 5,7-di | 176.176 | 0.24 | 124.772 | ⊖ |
| 5171162 | 5,5'-( | 531.735 | 6.617 | 439.943 | ⊖ |
| 4803280 | (4S)- | 341.402 | 4.016 | 268.061 | ⊖ |

Methods

| Method Name | Mobile Phase | Temperature | Flow Rate | Gradient Method | Wavelength | Instrument Name | Info |
|---|---|---|---|---|---|---|---|
| 406_CWP_1009_Halo_6 | A 0.05% TFA in Water | 50 | 0.7 | yes | 220 | A1100 | ⊖ |
| 812_GOJ_1032_halo_S5_IPCv5 | A=10mM Ammonium | 35 | 0.6 | yes | 265 | A1100 | ⊖ |

Runs

| Sample Name | Column Name | Vial | Injection ID | Run Date | Scientist | Run Time | Injection Volume | Info |
|---|---|---|---|---|---|---|---|---|
| Blank | Halo C18 3.0x100; | 61 | 74648 | Sep 29, 2009 | frierm | 25 | 5 | ⊖ |
| 100% AG-028303 STD | Halo C18 3.0x100; | 30 | 66127 | Sep 22, 2009 | frierm | 25 | 5 | ⊖ |
| 3.0% PF-3376629 | Halo C18 3.0x100; | 47 | 67072 | Sep 22, 2009 | frierm | 25 | 5 | ⊖ |

FIG. 4

Method Details

| | |
|---|---|
| Method Name: | 406_CWP_1009_Halo_6 |
| Mobile Phase: | A 0.05% TFA in Water |
| | B 0.05% TFA in ACN |
| Temperature: | 50 |
| Flow Rate: | 0.7 |
| Gradient Method: | Yes |
| WaveLength: | 220 |
| Instrument Name: | A1100 |

FIG. 5

Structure Details

*Structure Properties*

| | |
|---|---|
| Compound: | |
| IUPAC Name: | |
| Formula: | |
| Weight: | 177.2 |
| CLogP: | 1.325 |
| #H Bond Donor: | 3 |
| #H Bond Acceptor: | 1 |
| Molar Volume: | 150.591 |

*LogD*

| pH | LogD |
|---|---|
| 1 | 1.8 |
| 2 | 1.8 |
| 3 | 1.8 |
| 4 | 1.8 |
| 5 | 1.8 |
| 6 | 1.8 |

*pKa*

| Label | pKa | Confidence |
|---|---|---|
| Most Acidic | 12.78 | 0.4 |
| Less Acidic | | |
| Least Acidic | | |
| Least Basic | | |
| Less Basic | | |
| Most Basic | | |

FIG. 6

Method Search Results

Welcome, kate! Logout     Return to search

Structure Properties

| Compound | | IUPAC Name | Weight | CLogP | Molar Volume | Info |
|---|---|---|---|---|---|---|
| 88850 | | 4-methyl-3-vinylpyridine | 119.164 | 1.868 | 124.88 | ⊖ |
| 9111 | | 3-vinylpyridine | 105.137 | 1.369 | 108.605 | ⊖ |

Methods

| Method Name | Mobile Phase | Temperature | Flow Rate | Gradient Method | Wavelength | Instrument Name | Info |
|---|---|---|---|---|---|---|---|
| JPE_GC207_IM | | 100 | | | | 6890 | ⊖ |
| JPE_GC207_IM | | 100 | | | | 6890 | ⊖ |

Runs

| Sample Name | Column Name | Vial | Injection ID | Run Date | Scientist | Run Time | Injection Volume | Info |
|---|---|---|---|---|---|---|---|---|
| MVP STD - 7 Day Ambient | | 67 | 45647 | Aug 26, 2009 | ewersj | 22 | 1 | ⊖ |
| MVP Oxalate -100% - 1 - 7 Day Ambient | | 69 | 45720 | Aug 25, 2009 | ewersj | 22 | 1 | ⊖ |
| MVP Oxalate -100% - 1 - 7 Day Ambient | | 69 | 45797 | Aug 25, 2009 | ewersj | 22 | 1 | ⊖ |
| MeOH | | 65 | 46003 | Aug 25, 2009 | ewersj | 22 | 1 | ⊖ |
| MeOH | | 65 | 45597 | Aug 25, 2009 | ewersj | 22 | 1 | ⊖ |

FIG. 9

SYSTEMS, METHODS, AND APPARATUS FOR FACILITATING CHEMICAL ANALYSES

CROSS-REFERENCE TO RELATED APPLICATION

This application claims priority to and the benefit of, and incorporates herein by reference in its entirety, U.S. Provisional Patent Application No. 61/384,822, which was filed on Sep. 21, 2010.

TECHNICAL FIELD

In various embodiments, the present invention relates to systems, methods, and apparatus for facilitating chemical analyses. More specifically, described herein are exemplary systems, methods, and apparatus for determining methodologies, and the parameters thereof, to separate substances.

BACKGROUND

A typical day for an analytical chemist often includes performing a variety of chemical analyses, including the development of methodologies and procedures to separate mixtures of compounds in reaction batches, the deconvolution of degradation products, and/or the validation of product specifications. The methodologies used to analyze and separate mixtures of chemical compounds generally involve various machine settings, detector settings, and materials suitable to perform the separation. Unfortunately, to determine an appropriate methodology to be utilized in separating one or more chemical compounds from a sample, the analytical chemist typically has to employ a time-consuming and costly trial and error process utilizing his or her own experience and training.

The results of the analytical chemist's method runs may be stored in, for example, a scientific data management system (SDMS), a laboratory information management system (LIMS), or in any of a variety of other databases or digital library systems. However, using existing systems, the analytical data is often stored in such a way that very few other analytical chemists, even within the same laboratory, are able to thereafter effectively reuse the methodologies from those historical experiments, procedures, and/or processes.

For example, when wanting to separate a molecule that an analytical chemist in a laboratory worked with several months prior, another analytical chemist within that laboratory will typically undertake another time-consuming and costly trial and error process to determine the appropriate machine settings, detector settings, and materials to perform the separation. Complicating matters is the fact that data from previous separation runs are normally stored on a variety of different machines used in the laboratory, making it more difficult to determine what separation methodologies were successfully employed in the past.

As such, needs exist for improved procedures for facilitating chemical analyses, such as the development of separation methodologies, the deconvolution of degradation products, and the validation of product specifications.

SUMMARY OF THE INVENTION

Described herein are various embodiments of systems, methods, and apparatus that eliminate the trial and error process for analytical chemists in, for example, identifying appropriate methodologies for separating mixtures of compounds, deconvolving degradation products, and/or validating product specifications. In one embodiment, a knowledge management platform is provided that allows scientists, such as analytical chemists, to perform a variety of searches on data existing from previous experiments, procedures, and/or processes that may have been stored in a disorganized manner in order to find the best methodology to separate molecules. Advantageously, the platform connects methodologies, structures, and parameters that may be scattered across disparate, and physically separate, information stores, and may present to the user thereof (e.g., the analytical chemist) a single, searchable repository. As such, the platform may be employed to make faster decisions, and ultimately decreases the time taken in selecting an appropriate methodology.

In general, in one aspect, embodiments of the invention feature an apparatus for electronically identifying a separation method for separating one or more chemical compounds in a sample. The apparatus includes a memory for storing a relational database, a memory for storing a code defining a set of instructions, and a processor for executing the set of instructions. The code may include a search module. The memory for storing the relational database may be the same or a different memory from that which is used for storing the code.

The relational database includes data harvested from one or more other databases (e.g., a laboratory information management system (LIMS), a scientific data management system (SDMS), an electronic laboratory notebook, another relational database, a web page, and/or a searchable text file) that contain(s) experimental run data from completed separation experiments. The data in the relational database may be actively accessed from the one or more other databases, or the data may be copied from the one or more other databases into a consolidated database (i.e., the relational database). A set of separation method properties and a set of separation run properties from the harvested data are linked in the relational database to each of a plurality of chemical structure objects corresponding to one or more compounds separated in the completed separation experiments, and each of the one or more chemical structure objects is associated with a corresponding set of chemical structure properties in the relational database. The correlated separation method properties, separation run properties, and chemical structure properties are indexed and stored in the relational database.

For its part, the search module is configured to identify and display one or more chemical structures and corresponding separation method properties, separation run properties, and, optionally, chemical structure properties, in response to a user query of the relational database.

In various embodiments, the user query comprises two or more chemical structures or substructures as input, and the search module is configured to identify and display separation method properties and separation run properties common to all of the two or more chemical structures or substructures.

In one embodiment, the separation method properties include one or more text-based, numeric, and/or alphanumeric strings and/or ranges, such as a method name, a mobile phase indicator, a temperature, a temperature range, a flow rate, a flow rate range, a gradient method indicator, a wavelength, a wavelength range, an instrument name, a column name, a column particle size, a column length, and a column internal diameter. The separation run properties may include one or more text-based, numeric, and/or alphanumeric strings and/or ranges, such as a sample name, a vial number, a run date, a run date range, a process date, a process date range, a scientist name, a run time, a run time range, an injection number, an injection number range, an injection volume, and an injection volume range. For their part, the chemical structure properties may include one or more text-based, numeric, and/or alphanumeric strings and/or ranges, such as a compound number, a compound name, an IUPAC name, a molecular weight, a molecular weight range, a CLogP, a CLogP range, a molar volume, and a molar volume range.

In one embodiment, the search module is configured to identify and display via a graphical user interface, in response to the user query, a plurality of graphical representations of chemical structures from the relational database corresponding to one or more of: (A) a user-identified structure, (B) one or more substructures within the user-identified structure, (C) one or more structures containing the user-identified structure as a substructure therein, (D) one or more structures that are chemically similar to the user-identified structure, and/or (E) one or more structures corresponding to chemical compounds separated using separation method properties, separation run properties, and/or chemical structure properties identified in the user query. In addition, the search module may be further configured to, upon selection by the user of one of the chemical structures that are graphically represented on the graphical user interface, identify and display the separation method properties, separation run properties, and, optionally, chemical structure properties from the relational database corresponding to the user-selected chemical structure.

In another embodiment, the search module is further configured to archive data corresponding to the user query and query results in the relational database, thereby facilitating later data retrieval in response to a future user query.

In general, in another aspect, embodiments of the invention feature a procedure for electronically identifying a separation method for separating one or more chemical compounds in a sample. The procedure includes harvesting data from one or more databases (e.g., a laboratory information management system (LIMS), a scientific data management system (SDMS), an electronic laboratory notebook, a relational database, a web page, and/or a searchable text file) that contain(s) experimental run data from completed separation experiments. The procedure also includes correlating a set of separation method properties and a set of separation run properties from the harvested data with one or more chemical structure objects corresponding to one or more compounds separated in the completed separation experiments. Each of the one or more chemical structure objects is associated with a corresponding set of chemical structure properties. In addition, the procedure includes indexing and storing the correlated separation method properties, separation run properties, and chemical structure properties in a relational database, and displaying one or more chemical structures and corresponding separation method properties, separation run properties, and, optionally, chemical structure properties, in response to a user query of the relational database.

In various embodiments, the user query includes two or more chemical structures or substructures as input, and the separation method properties and separation run properties common to all of the two or more chemical structures or substructures are displayed in response to the user query.

In one embodiment, the separation method properties include one or more text-based, numeric, and/or alphanumeric strings and/or ranges, such as a method name, a mobile phase indicator, a temperature, a temperature range, a flow rate, a flow rate range, a gradient method indicator, a wavelength, a wavelength range, an instrument name, a column name, a column particle size, a column length, and a column internal diameter. The separation run properties may include one or more text-based, numeric, and/or alphanumeric strings and/or ranges, such as a sample name, a vial number, a run date, a run date range, a process date, a process date range, a scientist name, a run time, a run time range, an injection number, an injection number range, an injection volume, and an injection volume range. For their part, the chemical structure properties may include one or more text-based, numeric, and/or alphanumeric strings and/or ranges, such as a compound number, a compound name, an IUPAC name, a molecular weight, a molecular weight range, a CLogP, a CLogP range, a molar volume, and a molar volume range.

In one embodiment, displaying the one or more chemical structures and corresponding separation method properties, separation run properties, and, optionally, chemical structure properties, in response to the user query of the relational database, includes displaying via a graphical user interface a plurality of graphical representations of chemical structures from the relational database corresponding to one or more of (i) a user-identified structure, (ii) one or more substructures within the user-identified structure, (iii) one or more structures containing the user-identified structure as a substructure therein, (iv) one or more structures that are chemically similar to the user-identified structure, and/or (v) one or more structures corresponding to chemical compounds separated using separation method properties, separation run properties, and/or chemical structure properties identified in the user query. Upon selection by the user of one of the chemical structures that are graphically represented on the graphical user interface, the separation method properties, separation run properties, and, optionally, chemical structure properties from the relational database corresponding to the user-selected chemical structure may be displayed.

In another embodiment, data corresponding to the user query and the query results is archived in the relational database, thereby facilitating later data retrieval in response to a future user query.

Elements of embodiments described with respect to a given aspect of the invention may be used in various embodiments of another aspect of the invention. For example, it is contemplated that features of dependent claims depending from one independent claim can be used in apparatus, systems, and/or methods of any of the other independent claims.

BRIEF DESCRIPTION OF THE DRAWINGS

The foregoing and other objects, aspects, features, and advantages of the invention will become more apparent and may be better understood by referring to the following description taken in conjunction with the accompanying drawings, in which:

FIG. 2 is an image of a method search screen for inputting method properties and run details, in accordance with an illustrative embodiment of the invention;

FIG. 4 is an image of a search results screen displaying chemical structures, structure properties, method properties, and run details, in accordance with an illustrative embodiment of the invention;

FIG. 5 is an image of a method properties screen displaying information associated with a particular method, in accordance with an illustrative embodiment of the invention;

FIG. 6 is an image of a structure details screen displaying information associated with a particular chemical structure, in accordance with an illustrative embodiment of the invention;

FIG. 9 is an image of a search results screen displaying the results for a search to find separation methods for two structures, in accordance with an illustrative embodiment of the invention.

DESCRIPTION

In general, in various embodiments, the present invention pertains to systems, methods, and apparatus for facilitating chemical analyses. In broad overview, in accordance with one embodiment of the invention, a user (e.g., an analytical chemist) employs a computing system to rapidly identify one or more methodologies appropriate for separating mixtures of compounds, deconvolving degradation products, and/or validating product specifications. In particular, in one embodiment, the computing system employs algorithms to connect together the discrete methodologies, structures, and parameters that may be scattered across otherwise unconnected databases, instruments, etc., and then suggests to the user the best method(s) to utilize in performing the separation and analytical analysis.

Figure 1:
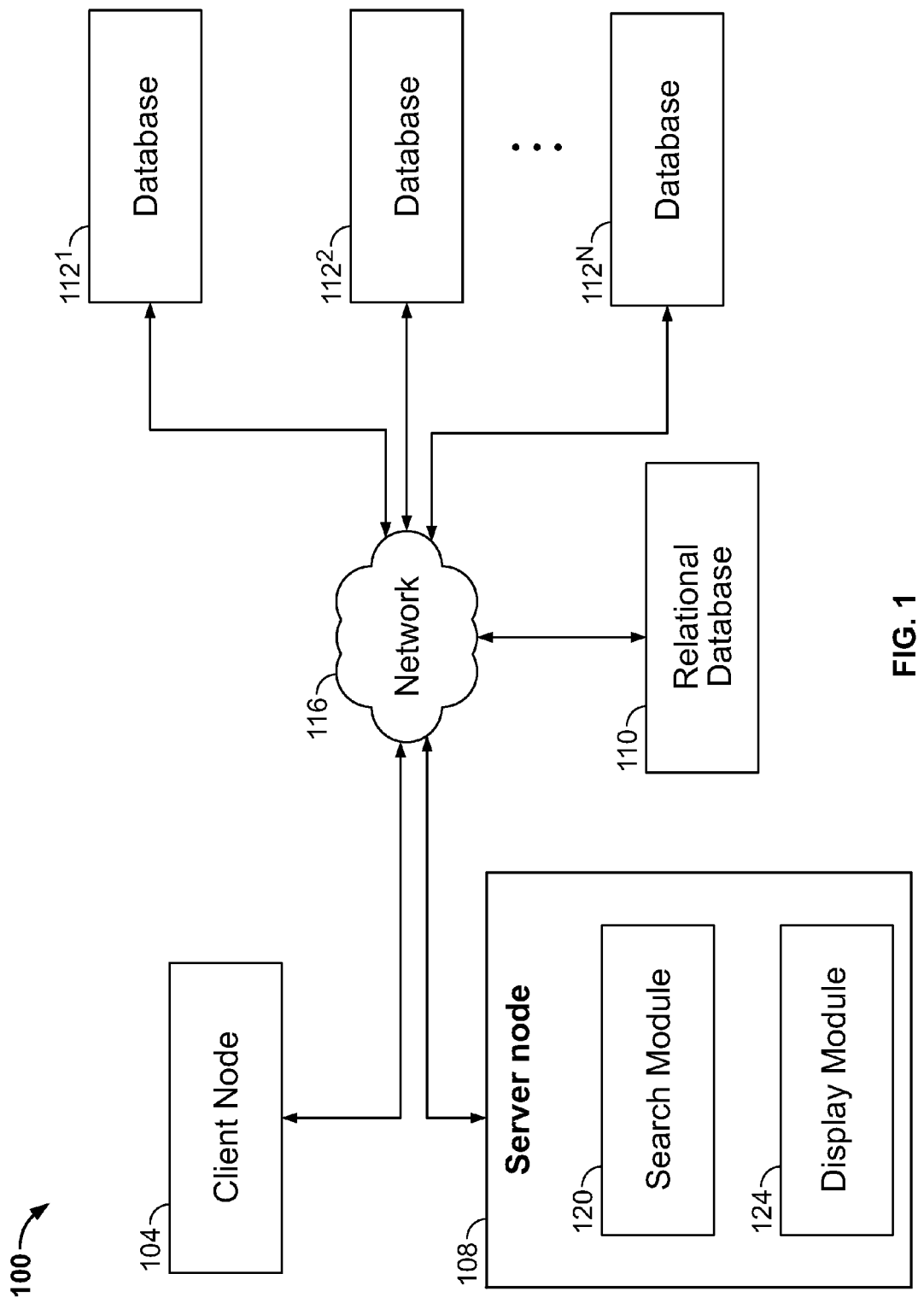
FIG. 1 is a block diagram of a system for facilitating chemical analyses in accordance with an illustrative embodiment of the invention.

FIG. 1 depicts a system 100, according to an illustrative embodiment of the invention, for facilitating chemical analyses. The system 100 includes a client node 104, a server node 108, a relational database 110, multiple additional databases $112^1$-$112^N$ (which, in one embodiment, are disparate and physically separate from one another), and, for enabling communications therebetween, a network 116. As illustrated, the server node 108 may include a search module 120 and a display module 124.

The network 116 may be, for example, a local-area network (LAN), such as a company or laboratory Intranet, a metropolitan area network (MAN), or a wide area network (WAN), such as the Internet. Each of the client node 104, server node 108, relational database 110, and additional databases $112^1$-$112^N$ may be connected to the network 116 through a variety of connections including, but not limited to, standard telephone lines, LAN or WAN links (e.g., T1, T3, 56 kb, X.25), broadband connections (e.g., ISDN, Frame Relay, ATM), or wireless connections. The connections, moreover, may be established using a variety of communication protocols (e.g., HTTP, TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g, and direct asynchronous connections).

The client node 104 may be any type of personal computer, Windows-based terminal, network computer, wireless device, information appliance, RISC Power PC, X-device, workstation, mini computer, main frame computer, personal digital assistant, set top box, handheld device, or other computing device that is capable of both presenting information/data to, and receiving commands from, a user of the client node 104 (e.g., an analytical chemist). The client node 104 may include, for example, a visual display device (e.g., a computer monitor), a data entry device (e.g., a keyboard), persistent and/or volatile storage (e.g., computer memory), a processor, and a mouse. In one embodiment, the client node 104 includes a web browser, such as, for example, the INTERNET EXPLORER program developed by Microsoft Corporation of Redmond, Wash., to connect to the World Wide Web.

For its part, the server node 108 may be any computing device that is capable of receiving information/data from and delivering information/data to the client node 104, for example over the network 116, and that is capable of querying, receiving information/data from, and delivering information/data to the relational database 110 and/or additional databases $112^1$-$112^N$. For example, as further explained below, the server node 108 may receive a search query from a user of the client node 104, query the relational database 110 and receive search results therefrom, and present the search results to the user at the client node 104. The server node 108 may include a processor and persistent and/or volatile storage, such as computer memory.

Each database $112^1$-$112^N$ may be any computing device that is capable of storing and managing collections of data, such as data relating to methodologies that may be used in separating mixtures of compounds. For example, each database $112^1$-$112^N$ may store experimental run data from completed separation experiments, such as appropriate machine settings, detector settings, and materials to perform the work. Each database $112^1$-$112^N$ may communicate using SQL or another language, or may use other techniques to store, receive, and transmit data.

As used herein, the term "database" is broadly used to refer to any repository of information. For example, a database $112^1$-$112^N$ may be a scientific data management system (SDMS), a laboratory information management system (LIMS), a relational database, an electronic laboratory notebook, or a computing device or any information store storing a web page, a searchable text file, PowerPoint slides, an Excel spreadsheet, etc. In addition, a database $112^1$-$112^N$ can be any information store storing the files output by an instrument used in chemical analyses, whether that be a computer memory onboard the instrument itself or a separate information store to which the output files of the instrument have been transferred. Exemplary instruments that may be used in chemical analyses include, but are not limited to, the Agilent 1100 instrument manufactured by Agilent Technologies of Santa Clara, Calif.; the Acquity HPLC, the Trizaic HPLC, and the Method Station X5 SFC manufactured by Waters Corporation of Milford, Mass.; the UltiMate 3000 HPLC manufactured by Dionex Corporation of Sunnyvale, Calif.; and the Flexar FX-15 UHPLC manufactured by Perkin Elmer of Waltham, Mass.

For its part, the relational database 110 is, in one embodiment, any computing device that is capable of receiving commands/queries and information/data from, and of delivering information/data to, the server node 108 and/or the client node 104. In one embodiment, the databases $112^1$-$112^N$ are disparate and physically separate databases, and the relational database 110 is a centralized database that stores and manages collections of data harvested from one or more of the databases $112^1$-$112^N$. Again, the relational database 110 may communicate using SQL or another language, or may use other techniques to store, receive, and transmit data.

The data stored within the relational database 110 may be harvested from the additional databases $112^1$-$112^N$ in any manner. For example, the data may be actively accessed from the additional databases $112^1$-$112^N$ or copied therefrom. In one embodiment, the harvesting is performed utilizing indexing and structure recognition algorithms, and the harvested data is connected together by examining and correlating the disjointed information that is found. For example, a set of separation method properties and a set of separation run properties (which are further described below) obtained from the harvested data may be linked in the relational database 110 to each of a plurality of chemical structure objects corresponding to one or more compounds that were separated in the completed separation experiments. The chemical structure objects may be, for example, of the type described in co-pending U.S. patent application Ser. No. 13/100,217 (e.g., computerized representations identifying various atoms, bonds, etc.), and each such chemical structure object may be associated with a corresponding set of chemical structure properties in the relational database 110. The entire content of co-pending U.S. patent application Ser. No. 13/100,217 is hereby incorporated herein by reference. Once the separation method properties, the separation run properties, and the chemical structure properties are correlated, they may then be indexed and stored in the relational database 110.

The search module 120 and the display module 124 of the server node 108 may each be implemented as any software program and/or hardware device, for example an application specific integrated circuit (ASIC) or a field programmable gate array (FPGA), that is capable of providing the functionality described below. It will be understood by one having ordinary skill in the art, however, that the illustrated modules 120 and 124, and the organization of the server node 108, are conceptual, rather than explicit, requirements. For example, the two illustrated modules 120 and 124 may be combined into a single module, such that the functions performed by the two modules 120 and 124, as described below, are in fact performed by the single module. In addition, it should be understood that any single one of the illustrated modules 120 and 124 may in fact be implemented as multiple modules, such that the functions performed by the single module, as described below, are in fact performed by the multiple modules.

Although not shown in FIG. 1, each of the client node 104, the server node 108, the relational database 110, and the additional databases $112^1$-$112^N$ may also include its own transceiver (or separate receiver and transmitter) that is capable of receiving and transmitting communications, including requests, responses, and commands, such as, for example, inter-processor communications and networked communications. The transceivers (or separate receivers and transmitters) may each be implemented as a hardware device, or as a software module with a hardware interface.

It will also be understood by those skilled in the art that FIG. 1 is a simplified illustration of the system 100 and that it is depicted as such to facilitate the explanation of the present invention's embodiments. Moreover, the system 100 may be modified in a variety of manners without departing from the spirit and scope of the invention. For example, rather than both being implemented on a single server node 108, the illustrated modules 120 and 124 may instead each be implemented on a different computing device (not shown) and such computing devices may communicate with one another directly, over the network 116, or over another additional network (not shown). In yet another example, the functionality of the relational database 110 may in fact be resident on the server node 108 (e.g., be implemented in the computer memory thereof). Additional options are for the server node 108 and/or the relational database 110 to be local to the client node 104 (such that they may all communicate directly without using the network 116), or for the functionality of the server node 108 and/or the relational database 110 to be implemented on the client node 104 (e.g., for the search module 120, the display module 124, and/or the relational database 110 to reside on the client node 104). As such, the depiction of the system 100 in FIG. 1 is non-limiting.

In certain embodiments, the system 100 accelerates the process of developing a method to separate chemical compounds by mining and utilizing existing data sets to suggest methods and procedures that work against new molecules requiring testing. For example, when a user executes a search for a desired chemical structure, the system 100 may display one or more separation methods that have been used previously to separate that structure. When the user selects one of these methods, the system 100 may then display one or more runs (e.g., tests, experiments, or measurements) that have been performed using that method. Each displayed structure, method, and/or run may include a link to one or more screens that display the details of the corresponding selection. The details may be viewed simultaneously so that a user can compare and contrast the differences between the individual runs, molecules, or methods from the plurality of choices resulting from the query. As previously described, the relational database 110 is obtained by harvesting information from a plurality of data sources. In general, the harvesting process occurs before correlation of the data, which may take place prior to populating the relational database 110. User querying, selection, and comparison activities generally occur after the relational database 110 has been populated.

In certain embodiments, the system 100 correlates individual substances (e.g., molecules, biologics, enzymes, and proteins) that were separated in a run (e.g., a test or measurement) to information contained in other systems that capture and track method and run data, but not substance data. While the substance data may be missing key components, the system 100 back-fills those missing components by crawling or searching ancillary systems that may not be related to method development or run execution, and by associating the information found in an amalgamated system that makes correlation of the run/method/substance information possible. A query engine is then layered upon the data so that users can query against this highly dimensional information in an easy to use manner. As further described below, the system 100 returns the results as a combination of visual images and tables that are combined and that interact with one another so that large volumes of this information can be filtered and visualized quickly.

A person or organization may use the system 100 to rationalize data and information from legacy systems. A user of the system 100 is able to query this data and information, run simulations, and/or develop hypotheses before any actual work commences.

While the system 100 may be used to target methods for separating substances, the general process and algorithms used by the system 100 for harvesting, indexing, and storing data, coupled with the advanced query and display technologies, can be applied to other methods. For the example, the system 100 may be used to search for food science methods, engineering methodologies, business process methodologies, and other business practices that follow a repetitive and complex workflow with many dimensions of data that are stored.

In certain embodiments, the system 100 produces a suggested method for use by the querying user. This method can then be applied to the real world process in a more efficient manner. The method can then be stored as an electronic record for future use or for use in a validated and/or controlled environment.

In certain embodiments, the systems, procedures, and apparatus described herein allow a user to search for the best method (e.g., a method of separating a chemical compound from a mixture) by querying the system 100 using a single search parameter or a combination of parameters. For example, referring to FIGS. 2 and 3, the system 100 allows the user to search by method properties, run details, and/or structure properties.

Figure 2:
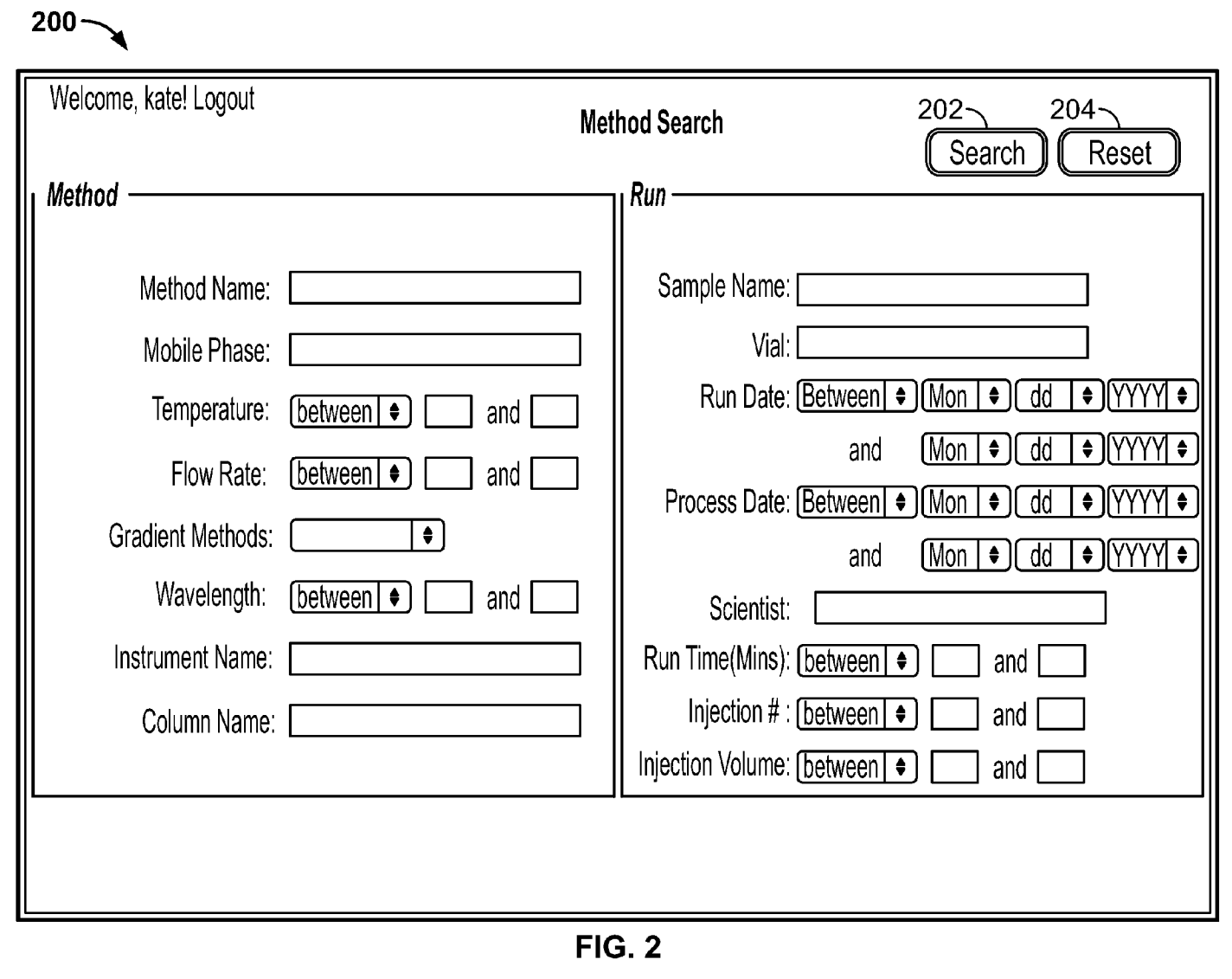

FIG. 2 is an image of a method search screen 200 for inputting method properties and run details, according to an embodiment of the invention. As depicted, method properties may include method name, temperature, mobile phase, flow rate, wavelength, gradient methods, column name, and/or instrument name. Additional method properties may include a column particle size, a column length, and/or a column internal diameter. Examples of method names include metabolite quantification, quality control of Guizhi Fuling capsules, multi-inlet TOF-MS, and KMD methylated. Temperatures, flow rates, and wavelengths (e.g., in mm) may be searched as numerical ranges. Gradient methods are typically searched as a yes or no choice. Instrument names are typically trade names or brand names of the instruments, such as A1100 (for the AGILENT 1100 instrument), ACQUITY HPLC, TRIZAIC HPLC, METHOD STATION X5 SFC, ULTIMATE 3000 UHPLC, and FLEXAR FX-15 UHPLC. Column names are typically trade names, such as CHIRALPAK ID, KINETEX PFP, KINETEX PHENYL-HEXYL, C8, C18, and STANDARD WIDEPORE C5. Sometimes a dimension will be included, such as LUNA 3 μm C18(2) 100 Å 150×4.6 mm and GEMINI-NX 5 μm C18 110 Å 150×4.6 mm. Run details may include sample name (typically a text string), vial (typically an alpha numeric string), run date, process date, scientist(s), run time, injection number, and/or injection volume.

In certain embodiments, the mobile phase may be any text based string. Examples of mobile phases that may be queried or utilized include HPLC grade water with 0.1% formic acid, and acetonitrile with 0.1% formic acid. These two examples include a solvent plus a buffer (i.e., formate as formic acid). Other possible buffers include phosphate, citrate, formate, acetate, tris(hydorxymethyl) aminomethane, ammonia, borate, and/or diethylamine. Any combination of the following exemplary mobile phase solvents may also be used: cyclohexane, n-hexane, 1-chlorobutane, carbon tetrachloride, i-propyl ether, toluene, diethyl ether, tetrahydrofuran, chloroform, ethanol, ethyl acetate, dioxane, methanol, acetonitrile, nitromethane, ethylene glycol, and water.

As depicted in FIG. 2, in certain embodiments, the method search screen 200 includes one or more dropdown menus, buttons, and/or cells or fields that the user may access to select or input search criteria using an input device, such as a mouse or keyboard. As depicted, the method search screen 200 includes a search button 202 that the user may select to begin a search. The method search screen 200 also includes a reset button 204 that the user may select to reset or clear the displayed search criteria.

Figure 3:
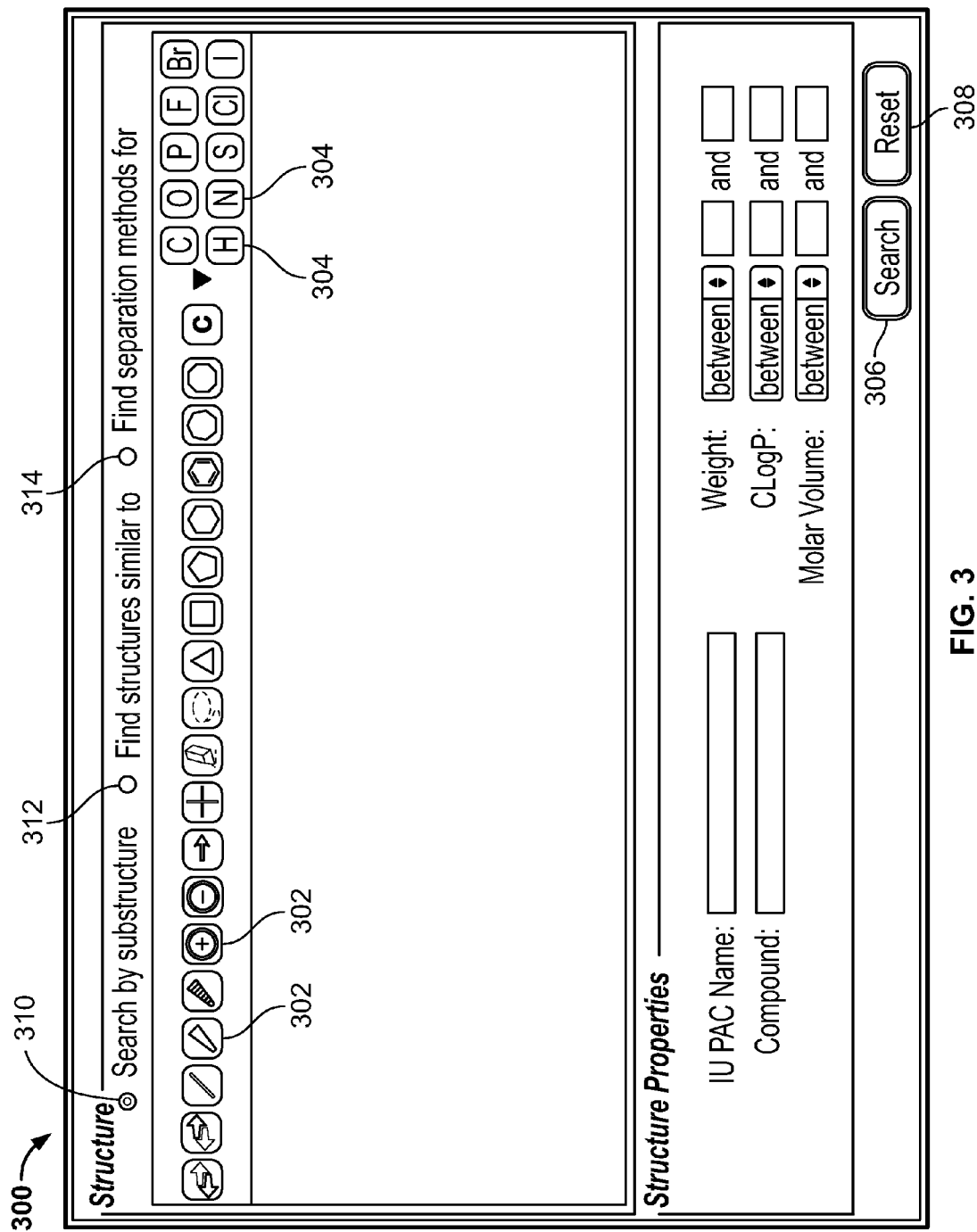
FIG. 3 is an image of a structure search screen for inputting one or more chemical structures and/or structure properties, in accordance with an illustrative embodiment of the invention.

FIG. 3 is an image of a structure search screen 300 for inputting one or more chemical structures and/or structure properties, according to an embodiment of the invention. As depicted, structure properties may include structure name (e.g., IUPAC name, or compound name), weight, cLogP, and molar volume. Additional structure properties may include LogD, melting point, boiling point, # of H donors or acceptors, pKa, and/or refraction index. In one embodiment, any combination of the method properties, run details, and structure properties may be entered by the user and searched by the system 100.

In certain embodiments, the structure search screen 300 includes structure buttons 302 and element buttons 304 that the user may select to build and display one or more chemical structures to be searched. For example, the user may add a benzene ring to a chemical structure by selecting a benzene ring button. Similarly, the user may add a nitrogen atom to a structure by selecting an "N" button. In another embodiment, structures may be copied or imported from other sources, such as CHEMDRAW, available from Perkin Elmer of Waltham, Mass. As depicted, the structure search screen 300 may include a search button 306 and a reset button 308 for initiating a search and resetting input data, respectively.

In certain embodiments, once the desired structure(s) has been created or obtained by the user, the system 100 allows the user to search (i) by substructure (i.e., the user can find methods through a substructure search), (ii) by similarity (i.e., the user can find methods through a similarity search of a drawn structure), or (iii) for separation methods for two or more structures (i.e., the user can request the system 100 to find the best methods for separating two or more drawn structures). Any of these searches may be performed with additional search criteria, such as one or more method properties and/or run details. Radio buttons may be selected by the user to identify the desired type of search. For example, in the embodiment depicted in FIG. 3, the user may select a first radio button 310 to search by substructure. In this case, the system 100 finds methods that have been used to separate structures having a desired substructure. Similarly, a second radio 312 button may be selected to search by similarity to find methods that have been used to separate similar structures. When evaluating the similarity of structures, the search module 120 may use, for example, a Tanimoto score and/or a Jaccard index. For example, the results may be ranked with a Tanimoto score indicating the similarity between the desired structure and the structures in the search results. A third radio button 314 may be selected to search for separation methods for two or more desired structures. With the third radio button 314 selected, the search module 120 will scan the relational database 110 to find methods for separating both of the drawn structures.

After the user has input the desired search criteria (i.e., method properties, run details, and/or structure properties), the user directs the system 100 to perform the search by selecting one of the search buttons 202, 306. The search module 120 then accesses the relational database 110 or the databases 112 and identifies search results that satisfy the search criteria. The display module 124 then displays the search results for the user. For example, the user may search for methods having a method name of "KMD Methylated." To perform this search, the user enters "KMD Methylated" in the method name cell of the method search screen 200. The user then selects the search button 202 and the system 100 returns all methods containing the name "KMD Methylated." Similarly, the user may search for runs (e.g., tests or measurements) associated with a particular injection number. After the user enters the desired injection number in the method search screen 200, the system 100 returns all runs associated with that injection number. As another example, the user may request a search for structures having a weight less than 300 daltons and cLogP less than 3.0, and the system 100 will identity structures that satisfy these criteria. In certain embodiments, any combination of method properties, run properties, and/or structure properties may be searched.

FIG. 4 is an image of a search results screen 400 depicting the results of a search for method names that include the term "halo," in accordance with one embodiment of the invention. As depicted, the search results include two methods 402 having "halo" in the method name. In addition to identifying these two methods, the system 100 returned run properties 404, structures 406, and structure properties 408 associated with the two methods. For example, the search results include images or graphical representations of structures 406 associated with the two methods. The search results also include details about the structure properties 408, the methods 402, and the run properties 404, associated with the two methods.

In another embodiment, the user may sort the tabulated results by selecting a column header.

In certain embodiments, the images of the structures 406 provided in the search results screen 400 may correspond to (A) a user-identified structure (e.g., a structure drawn by the user), (B) a substructure within the user-identified structure, (C) a structure containing the user-identified structure as a substructure therein, and/or (D) a structure that is chemically similar to the user-identified structure. In one embodiment, upon selecting an image of a structure 406, the system 100 displays additional information about the structure 406, such as separation method properties, separation run properties, and/or chemical structure properties, corresponding to the user-selected structure.

Figure 7:
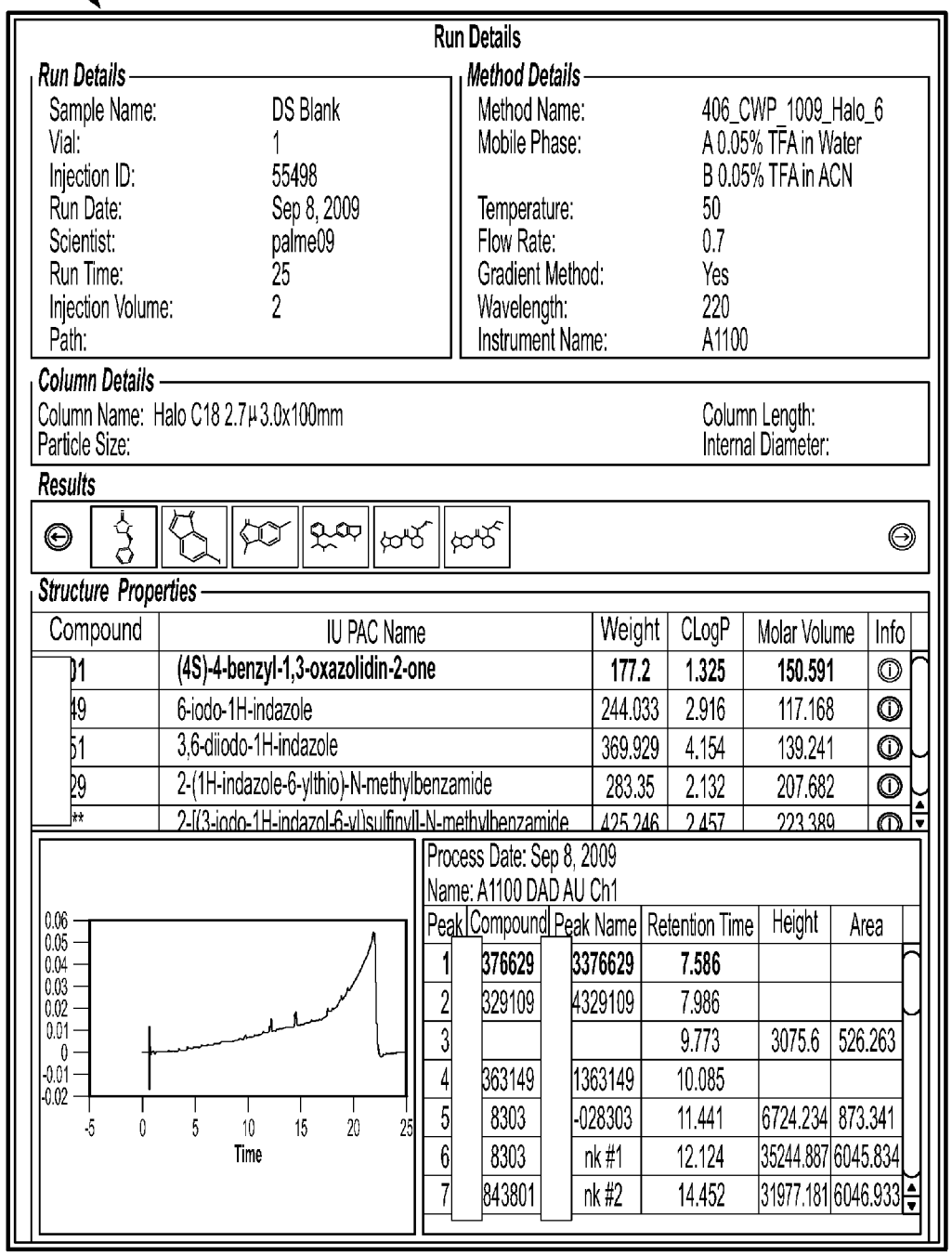
FIG. 7 is an image of a run details screen displaying information associated with a particular run, in accordance with an illustrative embodiment of the invention.

As depicted, in certain embodiments, the search results screen 400 includes information buttons 410 that the user may select to obtain additional, detailed information about the methods 402, run properties 404, or structures properties 408. In one embodiment, each information button 410 is associated with a row in the tabulated search results. For example, referring to FIG. 5, by selecting an information button 410 associated with a method in a row, the system 100 displays a method details screen 500 that includes detailed information about the method, such as the temperature and flow rate. Likewise, referring to FIG. 6, when an information button 410 associated with a structure is selected, the system 100 displays a structure details screen 600 that includes detailed information about the structure, including the name, weight, and molar volume. Further, referring to FIG. 7, when the user selects an information button 410 associated with a run, the system 100 displays a run details screen 700 that includes information about the run, including the sample name, date, and injection volume. In certain embodiments, the information displayed in FIGS. 5-7 can be viewed simultaneously so that the user can compare and contrast the differences of the individual runs, molecules, and/or methods from the plurality of choices resultant from the query.

Figure 8:
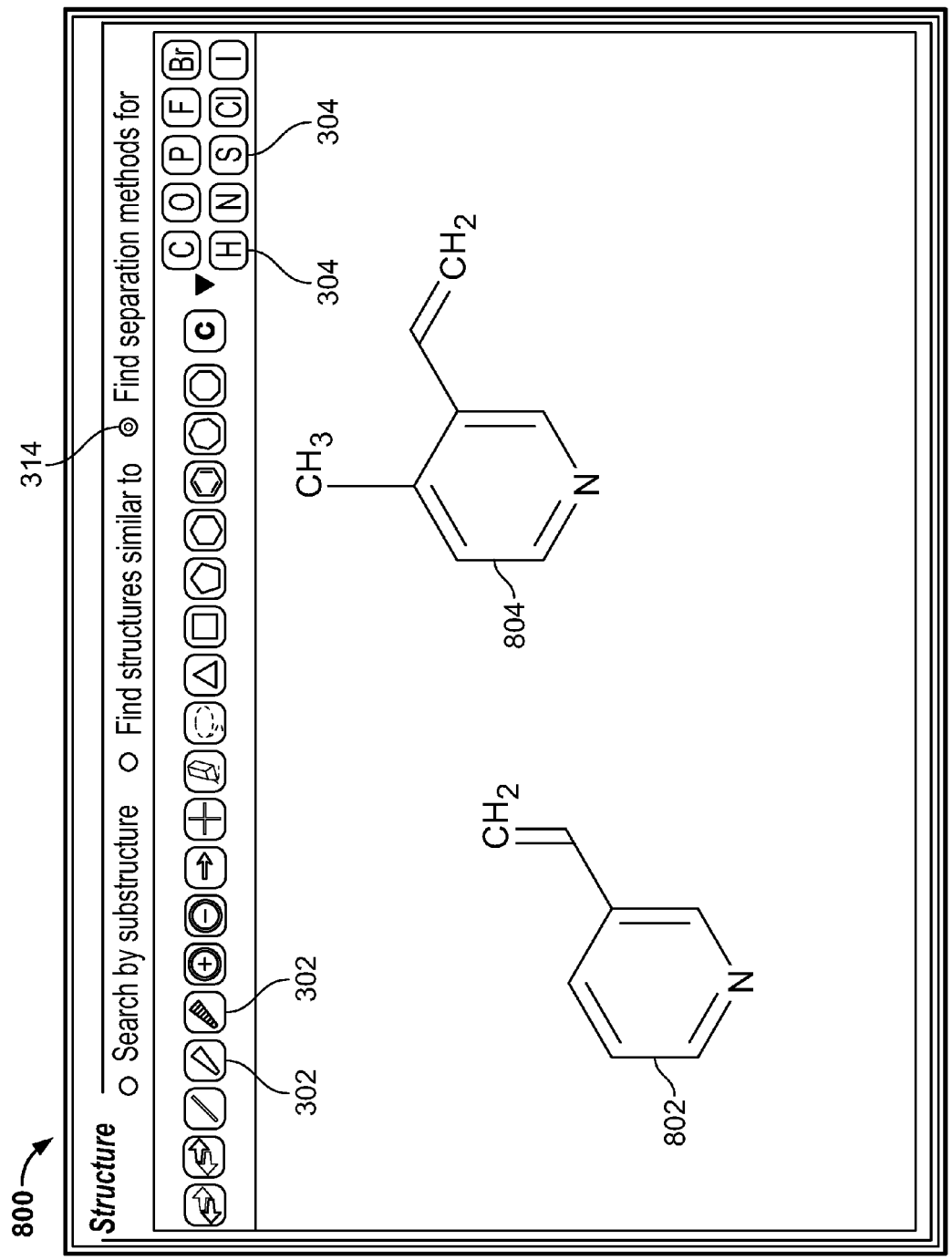
FIG. 8 is an image of a structure search screen displaying two chemical structures, in accordance with an illustrative embodiment of the invention.

FIGS. 8 and 9 depict a structure search screen 800 and a search results screen 900, respectively, associated with a search for methods that separate two or more structures, in accordance with one embodiment of the present invention. As depicted in FIG. 8, the user has drawn a first chemical structure 802 and a second chemical structure 804, using the structure buttons 302 and element buttons 304. The user has also selected the third radio button 314 to indicate that a search for methods that separate the two structures 802, 804 is desired. The results from the search are displayed in the search results screen 900 of FIG. 9. As depicted, the search results include methods 902 that may be used to separate the two structures. The search results also indicate method properties, run details 904, and structure properties 906, associated with the two structures 802, 804.

In certain embodiments, the system 100 identifies methods that separate two or more structures by identifying methods that were previously successful for separating each structure on its own. The system 100 then compares the method properties and run details for these previous methods and identifies a preferred method that includes method properties and run details that are common to each of the previous methods. For example, if a previous method for separating a first structure included a temperature range of 100° C. to 200° C., and a previous method for separating a second structure included a temperature range of 150° C. to 250° C., then the preferred method may include a temperature range of 150° C. to 200° C. (i.e., the region of overlap between the two previous temperature ranges).

In another embodiment, the system 100 archives search criteria and search results for later access by one or more users. For example, the system 100 may store, in the relational database 110, the method properties, run details, structure properties, and search results associated with a particular search. When a user wants to perform the same or similar search at a later date, the search parameters and/or search results may be retrieved before the additional search is conducted.

Accordingly, it can readily be seen that embodiments of the present invention provide a robust and powerful search application that, for example, facilitates the identification of appropriate methodologies for separating mixtures of compounds, deconvolving degradation products, and/or validating product specifications.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. An apparatus for electronically identifying a separation method for separating one or more chemical compounds in a sample, the apparatus comprising:
   a processor; and
   a memory having a set of instructions stored thereon, wherein the instructions, when executed by the processor, cause the processor to:
      receive a user query comprising a first chemical structure and a second chemical structure;
      access a relational database, wherein the relational database comprises
         substance data regarding a plurality of substances, wherein
            each substance of the plurality of substances comprises a respective set of chemical substance properties,
            and
         experimental run data from a plurality of completed separation experiments, wherein the experimental data comprises a set of separation method properties and a set of separation run properties,
wherein each separation method property of the set of separation method properties and each separation run property of the set of separation run properties is linked in the relational database to at least one respective chemical structure object of a plurality of chemical structure objects, wherein
each chemical structure object of the plurality of chemical structure objects corresponds to one or more compounds separated in a respective separation experiment of the plurality of completed separation experiments, and
wherein each chemical structure object of the plurality of chemical structure objects is linked in the relational database to a respective set of chemical structure properties associated with a particular substance of the plurality of substances;
identify, within the relational database, responsive to the user query, a) experimental data associated with separating the first chemical structure, and b) experimental data associated with separating the second chemical structure, wherein
the experimental data associated with separating the first chemical structure comprises at least one of separation method properties and separation run properties for separating the first chemical structure, and
the experimental data associated with separating the second chemical structure comprises at least one of separation method properties and separation run properties for separating the second chemical structure;
determine one or more common values common to both a) the experimental data associated with separating the first chemical structure, and b) the experimental data associated with separating the second chemical structure;
determine a preferred separation method for separating both the first chemical structure and the second chemical structure, wherein the preferred separation method comprises the one or more common values; and
provide, as at least a portion of query results presented to a user responsive to the user query, the preferred separation method.

2. The apparatus of claim 1, wherein:
each separation method property of the one or more separation method properties comprises
at least one value, wherein the at least one value comprises one or more of a text-based value, a numeric value, an alphanumeric value, and a value range, wherein
the at least one value identifies information selected from the group consisting of a method name, a mobile phase indicator, a temperature, a temperature range, a flow rate, a flow rate range, a gradient method indicator, a wavelength, a wavelength range, an instrument name, a column name, a column particle size, a column length, and a column internal diameter.

3. The apparatus of claim 1, wherein:
each separation run property of the one or more separation run properties comprises at least one value, wherein the at least one value comprises one or more of a text-based value, a numeric value, an alphanumeric value, and a value range, wherein
the at least one value identifies information selected from the group consisting of a sample name, a vial number, a run date, a run date range, a process date, a process date range, a scientist name, a run time, a run time range, an injection number, an injection number range, an injection volume, and an injection volume range.

4. The apparatus of claim 1, wherein:
each chemical structure property of the one or more chemical structure properties comprises at least one value, wherein the at least one value comprises one or more of a text-based value, a numeric value, an alphanumeric value, and a value range, wherein
the at least one value identifies information selected from the group consisting of a compound number, a compound name, an IUPAC name, a molecular weight, a molecular weight range, a CLogP, a CLogP range, a molar volume, and a molar volume range.

5. The apparatus of claim 1, wherein the instructions, when executed, further cause the processor to archive data corresponding to the user query and query results in the relational database, thereby facilitating later data retrieval in response to a future user query.

6. The apparatus of claim 1, wherein the one or more common values comprise an overlapping range of values between the experimental data associated with separating the first chemical structure and the experimental data associated with separating the second chemical structure.

7. The apparatus of claim 1, wherein the instructions, when executed, cause the processor to store the preferred method for future use.

8. A method comprising:
harvesting experimental run data from one or more databases containing the experimental run data from a plurality of completed separation experiments, wherein
the data comprises a set of separation method properties and a set of separation run properties;
correlating, by a processor of a computing device, each separation method property of the set of separation method properties and each separation run property of the set of separation run properties with a respective chemical structure object of one or more chemical structure objects, wherein
the respective chemical structure object corresponds to one or more compounds separated in a respective separation experiment of the plurality of completed separation experiments;
correlating, by the processor, each chemical structure object of the one or more chemical structure objects with a respective set of chemical structure properties of a respective substance of a plurality of substances, wherein correlating comprises
identifying one or more missing components in available substance data of a relational database,
harvesting, via a network, the one or more missing components from one or more databases other than the relational database, wherein the one or more databases contain substance data, and
backfilling, within the relational database the available substance data with the one or more missing components; and
after correlating each separation method property, each separation run property, and each chemical structure object, indexing and storing, by the processor, the set of separation method properties and the set of separation run properties in the relational database.

9. The method of claim 8, wherein:
each separation method property of the one or more separation method properties comprises at least one value, wherein the at least one value comprises one or more of a text-based value, a numeric value, an alphanumeric value, and a value range, wherein
the at least one value identifies information selected from the group consisting of consisting of a method name, a mobile phase indicator, a temperature, a temperature range, a flow rate, a flow rate range, a gradient method indicator, a wavelength, a wavelength range, an instrument name, a column name, a column particle size, a column length, and a column internal diameter.

10. The method of claim 8, wherein:
each separation run property of the one or more separation run properties comprises at least one value, wherein the at least one value comprises one or more of a text-based value, a numeric value, an alphanumeric value, and a value range, wherein
the at least one value identifies information selected from the group consisting of a sample name, a vial number, a run date, a run date range, a process date, a process date range, a scientist name, a run time, a run time range, an injection number, an injection number range, an injection volume, and an injection volume range.

11. The method of claim 8, wherein:
each chemical structure property of the respective set of chemical structure properties comprises at least one value, wherein the at least one value comprises one or more of a text-based value, a numeric value, an alphanumeric value, and a value range, wherein
the at least one value identifies information selected from the group consisting of a compound number, a compound name, an IUPAC name, a molecular weight, a molecular weight range, a CLogP, a CLogP range, a molar volume, and a molar volume range.

12. The method of claim 8, wherein the one or more databases containing the experimental run data comprise at least one of the following: a laboratory information management system (LIMS), a scientific data management system (SDMS), an electronic laboratory notebook, a web page, and a searchable text file.

13. The method of claim 8, further comprising:
receiving a user query; and
responsive to the user query,
identifying query results, wherein the query results comprise one or more chemical structures, and
causing the display of the one or more chemical structures.

14. The method of claim 13, wherein each graphical representation of one or more graphical representations of the respective one or more chemical structures is configured, upon selection, to cause the display of at least one of respective separation run properties of the set of separation run properties and respective separation method properties of the set of separation method properties.

15. A non-transitory computer memory having instructions stored thereon, wherein the instructions, when executed, cause a processor to:
collect, from one or more first databases comprising data from a plurality of completed separation experiments, experimental run data, wherein
the experimental run data comprises a plurality of separation method properties, a plurality of separation run properties, and a plurality of substance identifiers identifying one or more substances separated within a respective separation experiment of the plurality of completed separation experiments;
collect, from one or more second databases comprising data regarding a plurality of substances, substance data, wherein
the substance data comprises information regarding the plurality of substances, wherein
the plurality of substances comprises one or more of molecules, biologics, enzymes, and proteins, and
each substance of the plurality of substances comprises a set of chemical structure properties, and
the one or more first databases are different than the one or more second databases;
import, by a processor of a computing device, the experimental run data and the substance data into a relational database, wherein importing the experimental run data and the substance data comprises
correlating the plurality of substances to a plurality of chemical structure objects, wherein
each chemical structure object of the plurality of chemical structure objects comprises a graphical representation of at least one of a chemical structure and a chemical sub-structure,
correlating the plurality of separation method properties to the plurality of chemical structure objects,
correlating the plurality of separation run properties to the plurality of chemical structure objects,
indexing the plurality of separation method properties, the plurality of separation run properties, and the plurality of substances, and
storing the plurality of separation method properties, the plurality of separation run properties, and the plurality of substances within the relational database;
after importing the experimental run data and the substance data into the relational database, receive a user query;
responsive to the user query,
identify query results, wherein the query results comprise data regarding two or more experiments involving at least one chemical structure identified by the user query, and
cause presentation of a side-by-side comparison display of at least a portion of the data regarding at least two experiments of the two or more experiments, wherein the side-by-side comparison display comprises one or more links to detail associated with each of the at least two experiments.

16. The computer memory of claim 15, wherein the instructions, when executed, further cause the processor to, prior to causing the presentation of the side-by-side comparison display:
cause the presentation of a plurality of graphical representations of chemical structures, wherein
the plurality of graphical representations of chemical structures represent one or more of: (A) a user-identified chemical structure, (B) one or more substructures within the user-identified chemical structure, (C) one or more structures containing the user-identified chemical structure as a substructure therein, (D) one or more chemical structures that are chemically similar to the user-identified chemical structure, and (E) one or more chemical structures corresponding to chemical compounds separated using at least one of a i) separation method property, ii) separation run property, and iii) chemical structure property identified by the user query; and receive an indication of selection by the user of a first graphical representation of the plurality of graphical representations of chemical structures; wherein causing the presentation of the side-by-side comparison display comprises causing the presentation of at least one of a) two or more separation method properties and b) two or more separation run properties responsive to receiving the indication of selection by the user, wherein the at least one of the a) two or more separation method properties and b) two or more separation run properties corresponds to a particular chemical structure represented by the first graphical representation.

17. The computer memory of claim 15, wherein the user query comprises a user-defined graphical representation of a chemical structure.

18. The computer memory of claim 17, wherein the instructions, when executed, further cause the processor to archive the user-defined graphical representation of the chemical structure, wherein archiving facilities subsequent querying using the user-defined graphical representation of the chemical structure.

19. The computer memory of claim 15, wherein the user query identifies two or more chemical structures, and the query results comprise one or more separation methods, wherein each separation method of the one or more separation methods comprise separation method properties identifying each chemical structure of the two or more chemical structures.

20. The computer memory of claim 15, wherein the instructions, when executed, further cause the processor to, responsive to the user query:

cause the presentation of one or more information buttons, wherein each information button of the one or more information buttons is configured, upon selection, to cause the presentation of at least one of a) respective chemical structure property details, b) method property details, and c) run property details.

* * * * *